(12) United States Patent
Whitfield

(10) Patent No.: US 7,670,346 B2
(45) Date of Patent: Mar. 2, 2010

(54) SPECIMEN RETRIEVAL APPARATUS

(75) Inventor: Kenneth H. Whitfield, New Haven, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 960 days.

(21) Appl. No.: 11/092,063

(22) Filed: Mar. 29, 2005

(65) Prior Publication Data

US 2006/0229639 A1   Oct. 12, 2006

(51) Int. Cl.
*A61B 17/24* (2006.01)

(52) U.S. Cl. ..................................... 606/114

(58) Field of Classification Search ................. 606/113, 606/114, 127, 159, 200
See application file for complete search history.

(56) References Cited

U.S. PATENT DOCUMENTS

| | | | |
|---|---|---|---|
| 30,417 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,744,363 A | 5/1988 | Hasson |
| 4,790,812 A | 12/1988 | Hawkins, Jr. et al. |
| 4,927,427 A | 5/1990 | Kriauciunas et al. |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,234,439 A | 8/1993 | Wilk et al. |
| 5,279,539 A | 1/1994 | Bohan et al. |
| 5,312,416 A | 5/1994 | Spaeth et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |

(Continued)

FOREIGN PATENT DOCUMENTS

DE          25796          8/1883

(Continued)

*Primary Examiner*—Kevin T Truong

(57) ABSTRACT

A specimen removal apparatus includes a pouch assembly fabricated from a flexible membrane, a pouch support, a drawstring having a knot and forming a noose disposed circumferentially around a mouth of the pouch assembly, an endoscopic tubular portion, and a drive rod. The pouch assembly includes a plurality of circumferentially disposed guide members advantageously circumferentially spaced apart to define gaps therebetween. The guide members are disposed in a circumferential pathway proximal to the mouth of the pouch assembly. When the drawstring is pulled, the knot is stopped at an end of a guide member and the noose is closed, thereby closing the mouth of the pouch assembly. The pouch assembly is detachable from the apparatus.

20 Claims, 6 Drawing Sheets

U.S. PATENT DOCUMENTS

| | | | |
|---|---|---|---|
| 5,368,545 A | 11/1994 | Schaller et al. | |
| 5,368,597 A | 11/1994 | Pagedas | |
| 5,370,647 A | 12/1994 | Graber et al. | |
| 5,465,731 A | 11/1995 | Bell et al. | |
| 5,480,404 A | 1/1996 | Kammerer et al. | |
| 5,486,182 A | 1/1996 | Nakao et al. | |
| 5,486,183 A | 1/1996 | Middleman et al. | |
| 5,499,988 A | 3/1996 | Espiner et al. | |
| 5,524,633 A | 6/1996 | Heaven et al. | |
| 5,535,759 A | 7/1996 | Wilk | |
| 5,611,803 A | 3/1997 | Heaven et al. | |
| 5,618,296 A | 4/1997 | Sorensen et al. | |
| 5,643,283 A | 7/1997 | Younker | |
| 5,645,083 A | 7/1997 | Essig et al. | |
| 5,647,372 A | 7/1997 | Tovey et al. | |
| 5,658,296 A | 8/1997 | Bates et al. | |
| 5,679,423 A | 10/1997 | Shah | |
| 5,735,289 A * | 4/1998 | Pfeffer et al. | 600/564 |
| 5,755,724 A | 5/1998 | Yoon | |
| 5,759,187 A | 6/1998 | Nakao et al. | |
| 5,769,794 A | 6/1998 | Conlan et al. | |
| 5,785,677 A | 7/1998 | Auweiler | |
| 5,788,709 A | 8/1998 | Riek et al. | |
| 5,792,145 A | 8/1998 | Bates et al. | |
| 5,814,044 A | 9/1998 | Hooven | |
| 5,836,953 A | 11/1998 | Yoon | |
| 5,853,374 A | 12/1998 | Hart et al. | |
| 5,895,392 A | 4/1999 | Riek et al. | |
| 5,906,621 A | 5/1999 | Secrest et al. | |
| 5,957,884 A | 9/1999 | Hooven | |
| 5,971,995 A * | 10/1999 | Rousseau | 606/114 |
| 5,980,544 A | 11/1999 | Vaitekunas | |
| 5,997,547 A | 12/1999 | Nakao et al. | |
| 6,004,330 A | 12/1999 | Middleman et al. | |
| 6,007,512 A | 12/1999 | Hooven | |
| 6,036,681 A | 3/2000 | Hooven | |
| 6,123,701 A | 9/2000 | Nezhat | |
| 6,152,932 A | 11/2000 | Ternström | |
| 6,162,235 A | 12/2000 | Vaitekunas | |
| 6,165,121 A | 12/2000 | Alferness | |
| 6,168,603 B1 | 1/2001 | Leslie et al. | |
| 6,228,095 B1 * | 5/2001 | Dennis | 606/114 |
| 6,277,083 B1 | 8/2001 | Eggers et al. | |
| 6,344,026 B1 | 2/2002 | Burbank et al. | |
| 6,348,056 B1 | 2/2002 | Bates et al. | |
| 6,350,266 B1 | 2/2002 | White et al. | |
| 6,350,267 B1 | 2/2002 | Stefanchik | |
| 6,383,196 B1 | 5/2002 | Leslie et al. | |
| 6,383,197 B1 | 5/2002 | Conlon et al. | |
| 6,406,440 B1 | 6/2002 | Stefanchik | |
| 6,409,733 B1 | 6/2002 | Conlon et al. | |
| 6,419,639 B2 | 7/2002 | Walther et al. | |
| 6,447,523 B1 | 9/2002 | Middleman et al. | |
| 6,471,659 B2 | 10/2002 | Eggers et al. | |
| 6,506,166 B1 | 1/2003 | Hendler et al. | |
| 6,508,773 B2 | 1/2003 | Burbank et al. | |
| 6,755,779 B2 | 6/2004 | Vanden Hoek et al. | |
| 6,780,193 B2 | 8/2004 | Leslie et al. | |
| 6,805,699 B2 | 10/2004 | Shimm | |
| 6,872,211 B2 | 3/2005 | White et al. | |
| 6,887,255 B2 | 5/2005 | Shimm | |

FOREIGN PATENT DOCUMENTS

| | | |
|---|---|---|
| DE | 8435489 | 12/1984 |
| DE | 3542667 | 6/1986 |
| FR | 1272412 | 8/1961 |
| WO | WO 93/15675 A | 8/1993 |
| WO | WO 2004/002334 | 1/2004 |

* cited by examiner

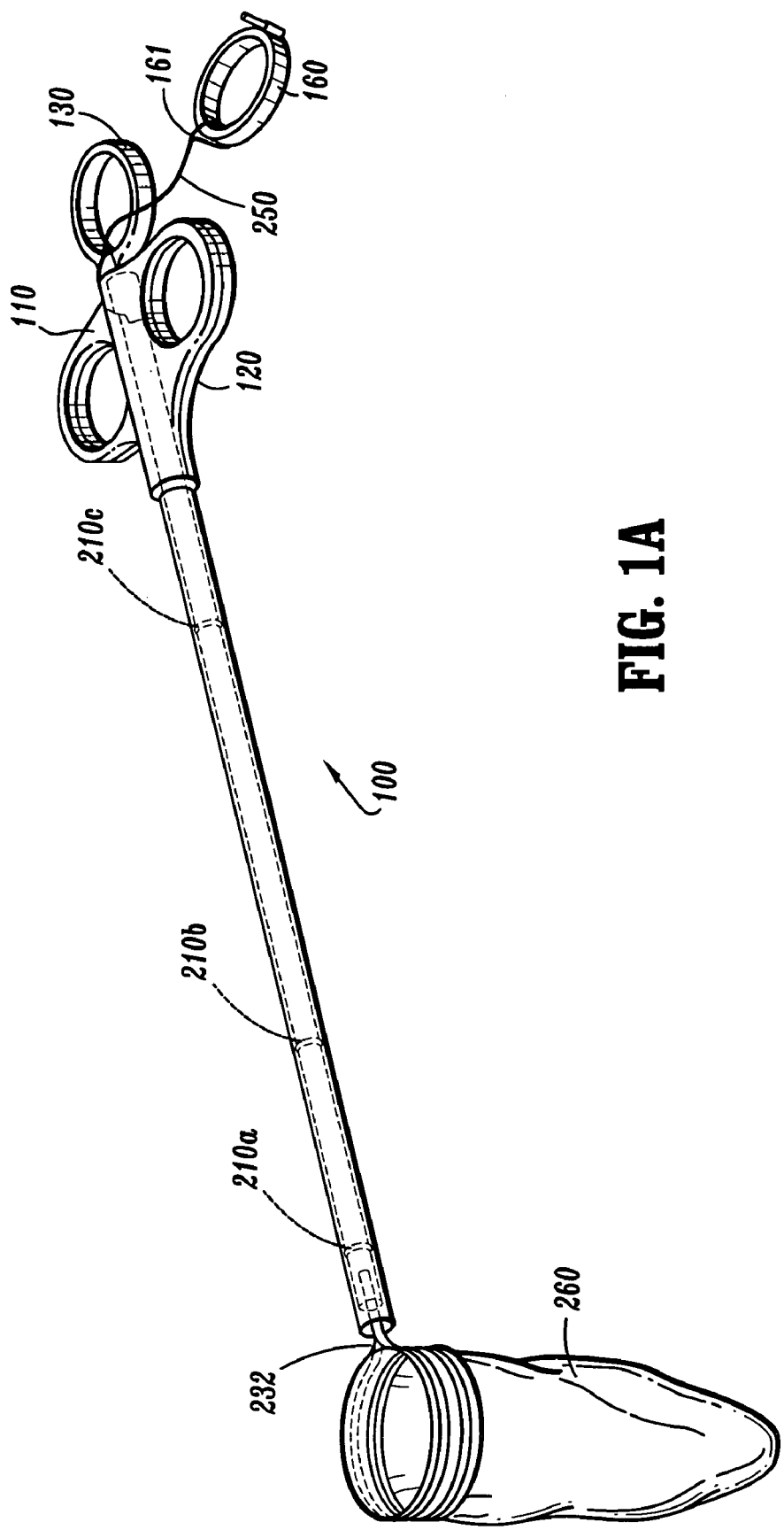

SPECIMEN RETRIEVAL APPARATUS

BACKGROUND

1. Field of the Invention

The present disclosure relates to a surgical containment apparatus. More particularly, the present disclosure relates to a specimen retrieval pouch for use in minimally invasive surgical procedures.

2. Background of the Art

Laparoscopic and endoscopic surgical procedures are minimally invasive procedures in which operations are carried out within the body by using elongated instruments inserted through small entrance openings in the body. The initial opening in the body tissue to allow passage of the endoscopic or laparoscopic instruments to the interior of the body may be a natural passageway of the body, or it can be created by a tissue piercing instrument such as a trocar. Laparoscopic and endoscopic procedures generally require that any instrumentation inserted in the body be sealed, i.e. provisions must be made to ensure that gases do not enter or exit the body through the instrument or the entrance incision so that the surgical region of the body, e.g. the peritoneum, may be insufflated. Mechanical actuation of such instruments is for the most part constrained to the movement of the various components along a longitudinal axis with structure provided to convert longitudinal movement to lateral movement where necessary.

Because the endoscopic or laparoscopic tubes, instrumentation, and any required punctures or incisions are relatively narrow, endoscopic or laparoscopic surgery is less invasive as compared to conventional surgical procedures in which the surgeon is required to cut open large areas of body tissue. Therefore, laparoscopic or endoscopic surgery minimizes trauma to the patient and reduces patient recovery time.

Minimally invasive procedures may be used for partial or total removal of body tissue or organs from the interior of the body, e.g. nephrectomy, cholecystectomy, and other such procedures. During such procedures, it is common that a cyst, tumor, or other affected tissue or organ must be removed via the access opening in the skin, or through a cannula. Various types of entrapment devices have been disclosed to facilitate this procedure.

For example, U.S. Pat. No. 5,037,379 to Clayman et al. discloses a surgical tissue bag for percutaneously debulking tissue by morcellation. The bag includes a layer of puncture-resistant material, a layer of moisture-resistant material and a drawstring. In a disclosed method of use, the bag is placed within the body cavity, the body tissue or organ is placed within the bag, the opening of the bag is pulled through the incision in the skin leaving the distal end of the bag containing the tissue or organ within the body cavity, a morcellator is then inserted into the bag, and then the tissue or organ is debulked and suctioned out of the bag.

U.S. Pat. No. 5,074,867 to Wilk discloses a planar membrane having filaments attached to its corners. The membrane is placed within a body cavity with the filaments extending through the trocar cannula to the outside of the body. The organ or tissue to be removed is placed on the membrane and the filaments are pulled to close the membrane around the organ and draw it through the cannula, if the organ is sufficiently deformable. If the organ is not sufficiently deformable, e.g. because of the presence of gallstones, a forceps or other instrument is used to crush the stones or tissue.

Another example is U.S. Pat. No. 6,409,733 to Conlon et al. Conlon et al. disclose a surgical retrieval bag having a row of alternating flexible and rigid sections proximal to the mouth of the bag. When a drawstring is tightened, the flexible sections buckle before the rigid sections allowing the bag to close in a predetermined manner.

In retrieval bags having a single, contiguous pathway for a drawstring or suture, the overall resistance to moving the drawstring through the pathway increases as the length of the pathway increases (i.e. the diameter of retrieval bag increases) since the outer surface of the drawstring and the inner surface of the pathway are in substantially constant contact with one another. As a result, additional forces may be required to move the drawstring through the pathway or the drawstring may stop moving through the pathway in response to the applied force.

SUMMARY

A surgical apparatus for removing tissue from an interior portion of a body during a surgical procedure is hereinafter disclosed. The surgical apparatus includes an elongate tubular member having an open distal end and a bore defined therein. In addition, the surgical apparatus includes a pouch assembly that is movable between a proximal location at least partially within the tubular member and a distal location at least partially exterior to the tubular member. The pouch assembly includes a support and a pouch that is removably attached to the support wherein the pouch has a first end movable between an open configuration and a closed configuration, and a closed second end. The pouch also includes a circumferential sleeve having a plurality of guide members wherein each guide member of the plurality of guide members has a passage. A drive member is disposed in the bore of the tubular member and is attached to the support for moving the pouch assembly from an undeployed position to a deployed position. A drawstring is disposed in the circumferential sleeve and extends through at least one passage of the guide members thereby forming a loop having a diameter corresponding to the diameter of the first end of the pouch.

The pouch may have at least a first sac with a first diameter and a second sac with a second diameter different than the first. The first sac may have an open distal end that is in communication with an open proximal end of the second sac. A reinforced region may be included that overlaps a distal end of the first sac and a proximal end of the second sac. The first diameter of the first sac may be greater than the second diameter of the second sac. The second sac can have a closed distal end. The apparatus may include a third sac having an open proximal end in communication with an open distal end of the second sac and the third sac can have a closed distal end. The support may be a spring that is biased toward a deployed position or may be a pair of flexible strips, each of the flexible strips having a first end attached to the drive member. Second ends of the flexible strips may be engaged by a joiner.

The surgical apparatus may also include a locking tab having a locking position that is in engagement with the drive member and a releasing position that is disengaged from the drive member. A handle may be disposed at a distal end of the tubular member and may slidably support the locking tab. The drawstring may include an actuator attached thereto for moving the first end of the pouch. The pouch can be formed from a sheet of substantially transparent material. The circumferential sleeve may include a lower circumferential sleeve for receiving the drawstring. The pouch may have an upper circumferential sleeve for receiving the support and may also include a weakened portion disposed between the upper and lower circumferential sleeves. The guide members may be spaced from one another within the lower circumferential sleeve.

BRIEF DESCRIPTION OF THE DRAWINGS

Embodiments of the present disclosure are described hereinbelow with reference to the drawings wherein:

FIG. 1A is a perspective view of a pouch assembly and a deployment apparatus according to an embodiment of the present disclosure;

DETAILED DESCRIPTION OF PREFERRED EMBODIMENT

As used herein with reference to the present disclosure, the terms "laparoscopic" and "endoscopic" are interchangeable and refer to instruments having a relatively narrow operating portion for insertion into a cannula or a small incision in the skin, or to a surgical procedure in which such instruments are employed. Use herein of the term "laparoscopic" should not be construed to exclude "endoscopic" and use herein of the term "endoscopic" should not be construed to exclude "laparoscopic." To the contrary, it is believed that the present disclosure may find use in any procedure where access to the interior of the body is limited to a relatively small incision, with or without the use of a cannula, including, but not limited to, laparoscopic procedures.

Figure 1B:
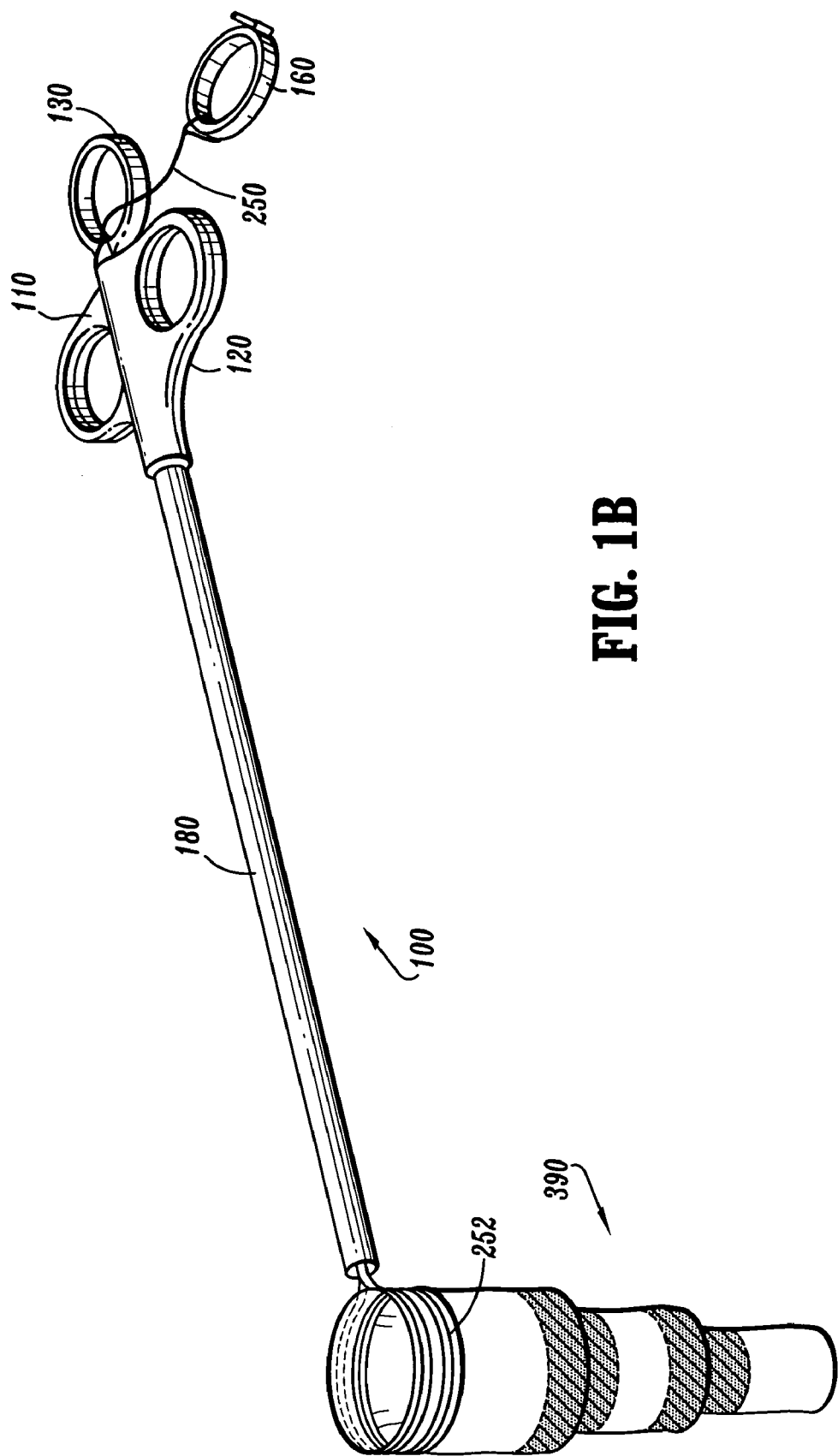
FIG. 1B is a perspective view of a pouch assembly and the deployment apparatus according to another embodiment of the present disclosure.
Figure 2:
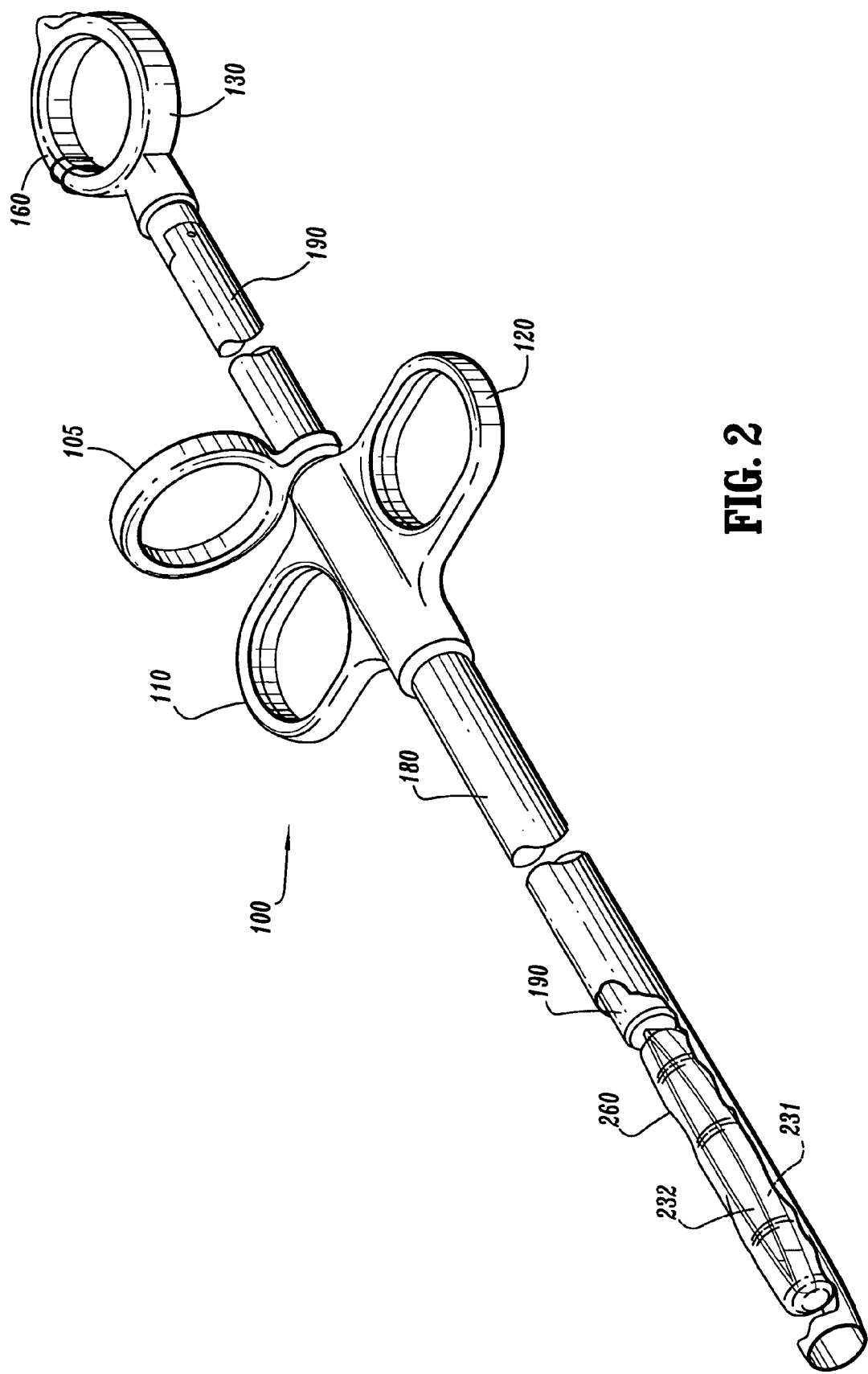
FIG. 2 is a perspective view of the apparatus in the initial, undeployed configuration.

An applicator assembly 100 is illustrated in FIGS. 1A, 1B, and 2. As shown in FIG. 1A, the applicator assembly 100 includes a first embodiment of a pouch assembly 260, while FIG. 1B illustrates the applicator assembly 100 with a second embodiment of a pouch assembly 390. An applicator assembly suitable for use in conjunction with either removal pouch assembly is disclosed in U.S. Pat. No. 5,647,372 to Tovey et al. and in U.S. Pat. No. 5,465,731 to Bell et al. and the entire contents of each is hereby incorporated by reference in their entirety.

The applicator assembly 100 includes an elongated tube 180 which is of such dimensions to be insertable through an access device, such as a trocar cannula, for endoscopic or laparoscopic procedures. The tube 180 is of such diameter as to permit it to be slidably disposed through a trocar cannula for use in endoscopic or laparoscopic operations, and is generally between about 0.25 inches to 0.50 inches in diameter, and about 10 inches to about 15 inches long, although other dimensions may also be used if appropriate to the operation being performed. Tube 180 slidably houses the drive rod 190 and, when undeployed, a support member 230 and pouch assembly 260. The support member 230 desirably comprises at least one flexible strip. Preferably, the support member 230 comprises a resilient spring. The resilient spring may be formed from two members of resilient material, each connected at one end to the drive rod 190 and connected to each other at the other end. A joiner or connector, such as a shrink tube, may be used to connect the resilient members. In the initial, unused condition, pouch assembly 260 will be rolled up and the support member 230, including support portions 231 and 232, will be relatively straight and positioned within tube 180. When the drive rod 190 is advanced, the support member 230 connected thereto will exit the distal end of tube 180 and resiliently pop open, thereby deploying and opening pouch assembly 260. Tube 180 is preferably formed from a metal such as stainless steel and is preferably coated with a shrink-wrap plastic such as shrinkable polyethylene fiberglass, or polyvinyl chloride of a grade suitable for use in surgical procedures.

The applicator assembly 100 includes a drive rod or bar 190 that is an elongated generally cylindrical member slidably disposed through the bore of tube 180. A distal end of the drive rod 190 is attached to the pouch assembly 260 to move the pouch assembly 260 from a non-deployed position contained within the outer tube 180 (as shown in FIG. 2) to a deployed position distal to the outer tube 180, (as shown in FIG. 1A). The drive rod 190 also includes O-rings 210a, 210b, and 210c. The O-rings help maintain a gaseous seal and/or help to maintain a drawstring in place while permitting sliding movement of the drive rod 190 through tube 180.

The drive rod 190 is preferably fabricated from a strong polymeric material. A material suitable for fabricating the drive rod 190 is polycarbonate plastic with 20% glass fiber filler. If gamma sterilization is desired, this material has the additional advantage of being gamma stable. Other materials suitable for the purposes discussed herein may also be used. To maintain a gaseous seal within the instrument, close tolerances are observed. The outer diameter of the drive rod 190 is slightly less than the inner diameter of the tube 180 through which it slides longitudinally. Additionally, the drive rod 190 is preferably coated with a biocompatible lubricant as a viscous sealing material to insure that no gases exit or enter the body through the seal when the operation site (e.g. the peritoneum or other body cavity) is insufflated. Any biocompatible lubricant that will operate as a viscous sealing material may be used, but if gamma sterilization is desired the biocompatible lubricant chosen should be gamma stable. A locking tab 105 (FIG. 2) is included to prevent premature actuation of the applicator assembly 100 during shipping. The locking tab 105 includes snap fit engagement structure to engage a slot of the drive rod 190. When thus engaged, the drive rod 190 cannot be pushed distally beyond the point where the locking tab 105 engages the proximal end of handle portions 110, 120. To actuate the applicator assembly 100 the surgeon must first disengage the locking tab 105 by pulling it off the applicator assembly 100.

In addition, the applicator assembly 100 includes a finger loop 130 for engagement by a user's finger. One end of a drawstring 250 is attached to the finger loop 130, as shown in FIGS. 1A and 1B while an opposing end of the drawstring 250 is attached to the pouch assembly 260 (see FIG. 3A).

Figure 3A:
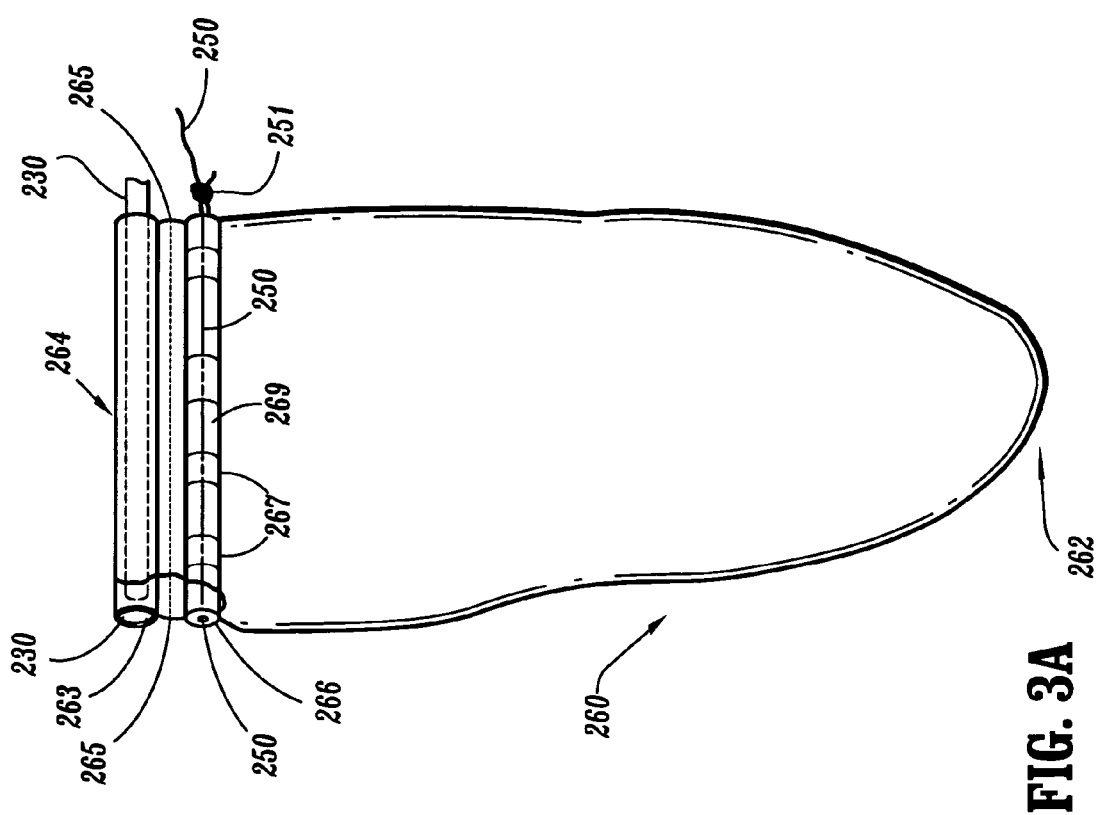
FIG. 3A is an elevational partially cut away view of the pouch assembly according to a first embodiment of the present disclosure.

Referring specifically to FIG. 3A, the pouch assembly 260 includes a flexible film or sheet preferably formed from a substantially transparent polymeric material. One preferred material is polyurethane sheet, although other biocompatible materials capable of forming a flexible membrane, such as latex, may be used. It is also preferred that the material selected be between about 0.001 to about 0.005 inches in thickness, although other ranges of thickness may be used as appropriate. Preferably, the material is transparent to permit viewing the contents of the pouch assembly 260. In a preferred configuration, the pouch assembly 260 is formed from an aromatic polyester type thermoplastic polyurethane such as Dureflex®, a product of Deerfield Urethane, Inc. in Whately, Mass. In addition, the sac material should be impervious to penetration by cancer cells.

The pouch assembly 260 may be of any dimensions suitable for the purpose of organ entrapment or removal. In the present embodiment, the pouch assembly 260 has a diameter of from about 1.5 inches to about 6.0 inches, a depth of from about 2 inches to about 10 inches, and has a cubic capacity of up to about 2.0 liters of water, depending upon the dimensions of the pouch assembly 260.

Pouch assembly 260 includes a closed distal end portion 262 and an openable and closable end portion or mouth 264. The pouch assembly 260 may alternatively include a circumferential concave portion 263 in the vicinity of the open proximal end portion or mouth 264, for facilitating rolling and placement of the pouch assembly 260 within an elongated tube 180 (See FIG. 2). The open proximal end portion or mouth 264 is defined by a proximal (upper) circumferential tubular portion or sleeve 263, and a distal (lower) circumferential tubular portion or sleeve 266, which are spaced apart from each other.

The pouch assembly 260 possesses a linear portion 265 weakened by perforation or, more preferably, scoring, which extends circumferentially around the mouth 264 of the pouch assembly 260 between the proximal and distal sleeves 263 and 266, respectively. The scored line 265 may be created by induction heating to create a linear portion having thickness less than that of the original material to facilitate tearing of the material along the scored line 265.

The proximal sleeve 263 is adapted to receive a support member 230, described below. The distal sleeve 266 is adapted to receive the drawstring 250. One end of the drawstring 250 may include a knot. The scored line 265 is adapted to tear when the drawstring 250 is pulled with sufficient force to close the mouth 264 of the bag distal to the scored line 265, thereby providing fast detachment of pouch assembly 260 from the support member 230 simultaneously with closure of mouth 264. Clearly, alternative structures also can be utilized to detach the pouch assembly 260 from the support member 230, such as by pulling with a grasper or by cutting with a scissors.

Figure 4:
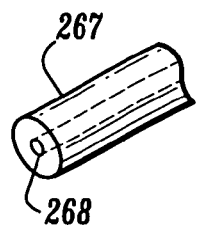
FIG. 4 is a perspective view of an end of a guide member according to an embodiment of the present disclosure.

Preferably, the distal sleeve 266 of the present disclosure includes a plurality of guide members 267. The distal sleeve 266 extends circumferentially around the mouth 264 of the pouch assembly 260 forming a loop or pathway for the drawstring 250. The drawstring 250 traverses through each of the guide members 267 by passing through each of the passage 268 to form a loop or noose around the mouth 264. The guide members 267 are circumferentially spaced apart from one another defining a plurality of gaps 269 therebetween as seen in FIG. 3A. Each guide member 267 has opposing first and second orifices defining a passage 268 therebetween (see FIG. 4). Each passage 268 is dimensioned for slidably receiving the drawstring 250 therethrough and is further dimensioned to act as a stop for the knot. The dimensions of the drawstring 250, the dimensions of the mouth 264, and other design and/or operating considerations may determine the number and arrangement of the guide members 267 and the corresponding gaps 269 included in the distal sleeve 266.

The distance the drawstring 250 travels around the circumference of the mouth 264 is substantially similar to that of similarly dimensioned retrieval bags having a substantially contiguous pathway. However, the advantageous spacing apart of the guide members 267 of the distal sleeve 266 reduces the amount of contact between the drawstring 250 and the passages 268 for as compared to the amount of contact a drawstring would encounter in a substantially contiguous pathway having the same circumferential travel distance. By reducing the total contact between the drawstring 250 and the passages 268, the embodiment of the present disclosure significantly reduces the total resistance to movement of the drawstring 250. Thusly, pulling the drawstring 250 to close the mouth 264 of the pouch assembly 260 requires a reduced amount of force as compared with similarly sized retrieval bags that have a substantially contiguous pathway or passage for guiding the drawstring around the mouth of a pouch assembly. Alternatively, the guide members 267 may include coatings and/or be formed from selected materials for minimizing friction.

Figure 3B:
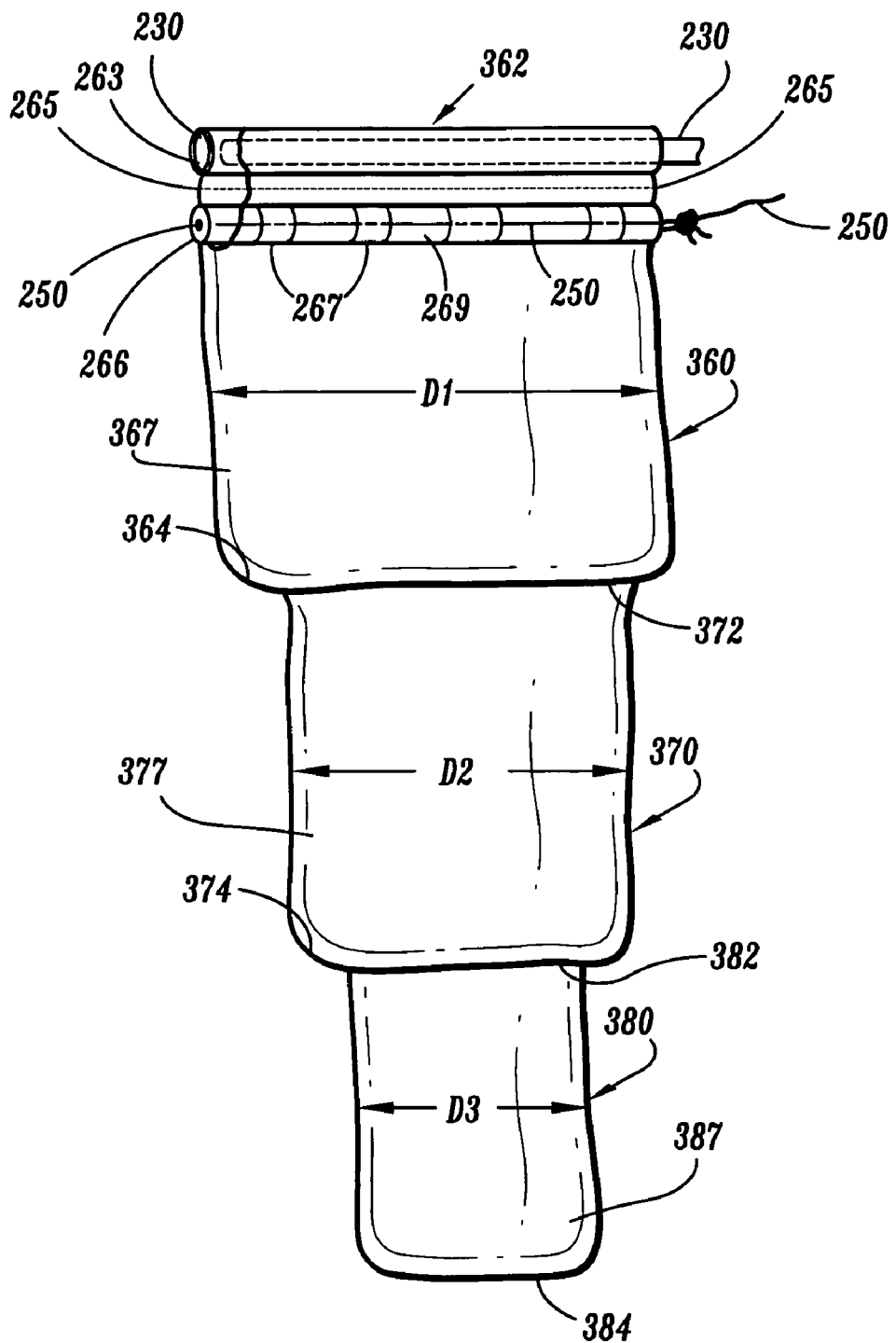
FIG. 3B is another embodiment of the pouch assembly of FIG. 3 according to a second embodiment of the present disclosure.

Referring to FIG. 3B, an alternate embodiment of the pouch assembly 390 includes a first sac 360, a second sac 370, and a third sac 380. Each sac is formed from a suitable material as discussed in the embodiment of FIG. 3A. In addition, the pouch assembly 390 may be of any dimensions suitable for the purpose of organ entrapment or removal as discussed in the embodiment of FIG. 3A.

The first sac 360 includes a mouth 362 and an orifice 364 at opposing ends defining a throat 367 therebetween. Preferably, the throat 367 has a diameter D1 that is substantially uniform from the mouth 362 to the orifice 364. Alternately, the first sac 360 may be tapered from the mouth 362 to the orifice 364 forming a frustoconical or an inverted frustoconical shape. In addition, other shapes and configurations of the sac are contemplated. The mouth 362 has an open and a closed configuration while the orifice 364 only has an open configuration.

In particular, the first sac 360 possesses a linear portion weakened by perforation or, more preferably, scoring, which extends circumferentially around the mouth 362 of the first sac 360 between proximal and distal sleeves 363 and 366, respectively. A scored line 365 may be created by induction heating to create a linear portion having thickness less than that of the original material to facilitate tearing of the material along the scored line 365.

Similar to the embodiment illustrated in FIG. 3A, the pouch assembly 390 is adapted to be attached to the support member 230 using the distal sleeve 266 and includes substantially identical structures for the attachment and separation of the pouch assembly 390. In addition, the preferred embodiments of the pouch assembly 390 include the spaced apart guide members 267 and the resulting gaps 269 of the previous embodiment with the resulting advantages discussed previously.

Still referring to FIG. 3B, the second sac 370 has a mouth 372 and an orifice 374 at opposing ends defining a throat 377 therebetween. Similar to the first sac 360, the second sac 370 has a diameter D2 that is substantially uniform from the mouth 372 to the orifice 374. Alternately, the second sac 370 may be tapered from the mouth 372 to the orifice 374 forming a frustoconical or an inverted frustoconical shape. In addition, other shapes and configurations of the sac are contemplated. The mouth 372 is open and in communication with the throat 367 of the first sac 360. It is preferred that the diameter D2 or the diameter of the mouth 372 is less than the diameter D1 or the diameter of the orifice 364. Configured thusly, the throats 367, 377 of the first and second sacs 360, 370, respectively, are in fluid communication with each other and form a staggered arrangement of the sacs included in the pouch assembly 390.

The third sac 380 includes a mouth 382 and a base 384 at opposing ends. The mouth 382 is open while the base 384 is closed defining a cavity 387 therein. The cavity has a diameter D3 that is preferably uniform throughout. Alternately, the third sac 380 may be tapered from the mouth 382 to the base 384 forming a frustoconical or an inverted frustoconical shape. In addition, other shapes and configurations of the sac are contemplated. The mouth 382 is in fluid communication with the throat 377 of the second sac 370. It is preferred that the diameter D3 or the diameter of the mouth 382 is less than the diameter D2 or the diameter of the orifice 374. In this configuration, the throats 367, 377, and 387 are in fluid communication with one another to form a staggered arrangement of the pouch assembly 390.

Figure 3C:
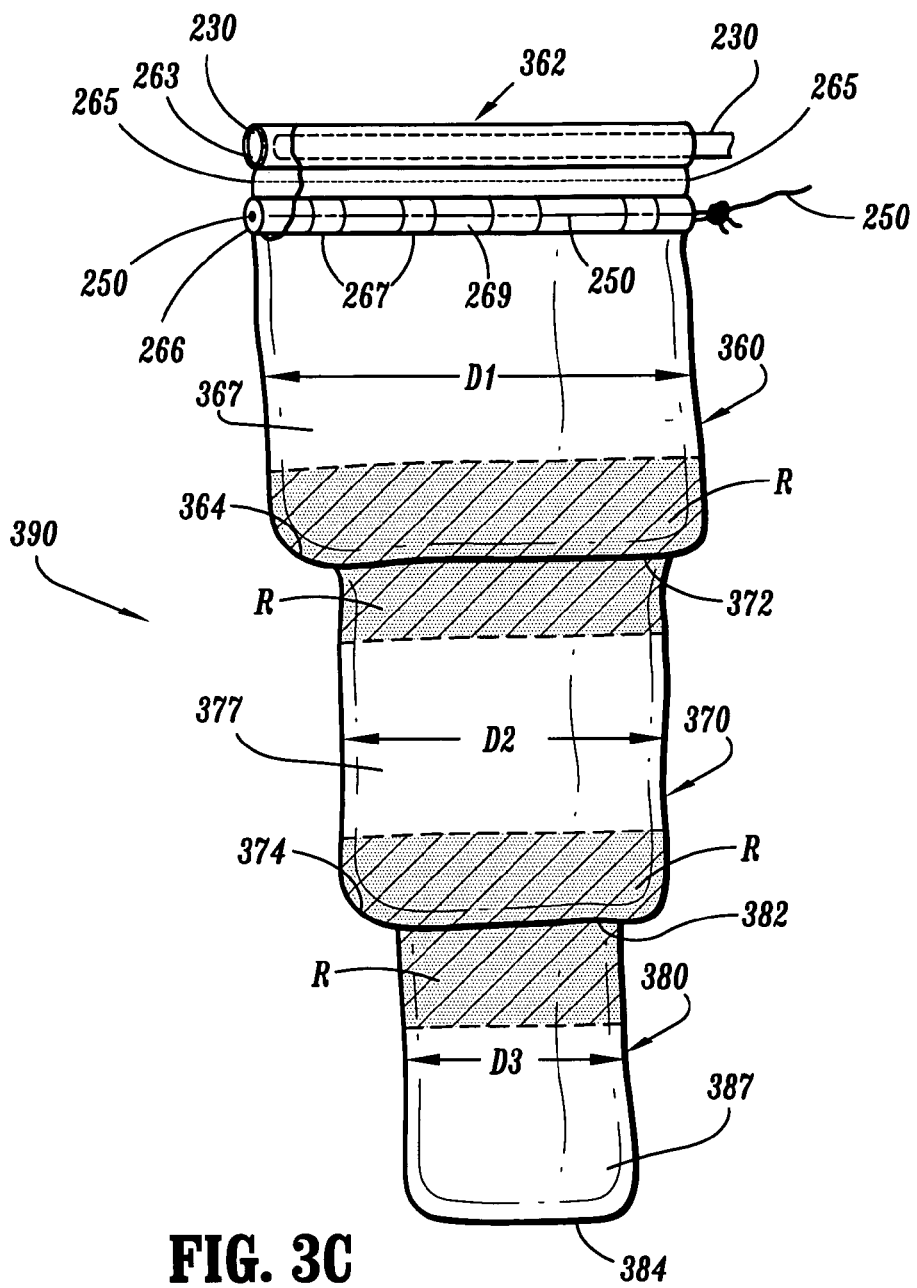
FIG. 3C is an alternate embodiment of the pouch assembly of FIG. 3B.

Referring now to FIG. 3C, an alternate embodiment of the pouch assembly 390 is disclosed. The pouch assembly 390 according to this embodiment includes the same or similar components as the embodiment shown in FIG. 3B and further includes a reinforced band or region R. The reinforced region R overlaps the junction between an orifice and a mouth of a pair of adjacent sacs (e.g. orifice 364 of sac 360 and mouth 372 of sac 370). The dimensions (i.e. thickness and/or height) of the reinforced region R may be influenced by a number of factors including, but not limited to, dimensions of the pouch assembly 390, dimensions of the adjoining sacs, and the task being performed. The reinforced region R improves the overall rigidity of the pouch assembly 390 and helps maintain the staggered or stepped shape of the pouch assembly 390. Additionally, the reinforced regions R improve the strength of the joint between the adjacent sacs thereby minimizing the possibility that the sacs will separate during a surgical procedure or increasing the size and/or mass of the tissue sample to be collected.

In preferred embodiments, the reinforced region R extends circumferentially about the pouch assembly 390 although it is contemplated that it may only extend for a portion of a circumference of the pouch assembly 390. Alternatively, the reinforced region R may include a plurality of reinforced sections that are circumferentially spaced apart forming gaps therebetween. It is preferred that each reinforced section have substantially identical dimensions (i.e. thickness, height, and width), although it is contemplated that the dimensions of the reinforced sections may be varied for the same or similar reasons discussed for the embodiment of FIG. 3B. As in the previous embodiment, the reinforced region R may extend circumferentially about the pouch assembly 390 or only for a portion thereof. In either of the embodiments of FIG. 3B or 3C, the reinforced region R may be included in some or all of the pairs of adjacent sacs.

Similar to the embodiment illustrated in FIG. 3B, the pouch assembly 390 is adapted to be attached to the support member 230 using the distal sleeve 266 and includes substantially identical structures for the attachment and separation of the pouch assembly 390. In addition, the preferred embodiments of the pouch assembly 390 include the spaced apart guide members 267 and the resulting gaps 269 of the previous embodiment with the resulting advantages discussed previously.

Alternatively, the pouch assembly 390 may only include two sacs where the second sac has a closed end opposite its mouth defining a cavity therein. In other embodiments of the disclosure, additional sacs may be included with the last or most distal sac having a closed end opposite its mouth to define a cavity therein. These alternative configurations increase the flexibility and utility of the pouch assembly 390 of the present disclosure. The pouch assembly 390 may be formed from discrete sacs where the sacs are bonded or joined together using known methods such that each bond is substantially fluid-tight. Alternatively, the pouch assembly 390 may be monolithically formed using known methods to create the staggered arrangement of the included sacs. The pouch assembly of these alternate embodiments may include reinforced bands or regions as previously discussed.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure.

What is claimed is:

1. A surgical apparatus for removing tissue from an interior portion of a body during a surgical procedure, comprising:
    an elongate tubular member having an open distal end and a bore defined therein;
    a pouch assembly movable between a proximal location at least partially within the tubular member and a distal location at least partially exterior to the tubular member, the pouch assembly including a support and a pouch removably attached to the support;
    the pouch having a first end movable between an open configuration and a closed configuration, and a closed second end;
    the pouch including a circumferential sleeve having a plurality of guide members, each guide member of the plurality of guide members having a passage and being configured to move toward adjacent guide members providing a variable space between guide members;
    a drive member disposed in the bore of the tubular member and attached to the support for moving the pouch assembly from an undeployed position to a deployed position; and
    a drawstring disposed in the circumferential sleeve, extending through at least one passage of the guide members, and forming a loop having a diameter corresponding with the diameter of the first end of the pouch.

2. The apparatus of claim 1, wherein the pouch has at least a first sac with a first diameter and a second sac with a second diameter different than the first.

3. The apparatus of claim 2, wherein the first sac has an open distal end in communication with an open proximal end of the second sac.

4. The apparatus of claim 3, further comprising a reinforced region overlapping a distal end of the first sac and a proximal end of the second sac.

5. The apparatus of claim 3, wherein the first diameter is greater than the second diameter.

6. The apparatus of claim 5, wherein the second sac has a closed distal end.

7. The apparatus of claim 5, further comprising a third sac having an open proximal end in communication with an open distal end of the second sac.

8. The apparatus of claim 7, wherein the third sac has a closed distal end.

9. The apparatus of claim 1, wherein the support comprises a spring biased toward a deployed position.

10. The apparatus of claim 1, wherein the support comprises a pair of flexible strips, each of the flexible strips having a first end attached to the drive member.

11. The apparatus of claim 10, wherein each of the flexible strips has a second end engaged by a joiner.

12. The apparatus of claim 1, further comprising a locking tab having a locking position in engagement with the drive member and a releasing position disengaged from the drive member.

13. The apparatus of claim 12, further comprising a handle at a distal end of the tubular member, the handle slidably supporting the locking tab.

14. The apparatus of claim 1, further comprising an actuator attached to the drawstring for moving the first end of the pouch.

15. The apparatus of claim 1, wherein the pouch comprises a sheet of substantially transparent material.

16. The apparatus of claim 1, wherein the circumferential sleeve comprises a lower circumferential sleeve for receiving the drawstring.

17. The apparatus of claim 16, wherein the pouch has an upper circumferential sleeve for receiving the support.

18. The apparatus of claim 17, wherein the pouch has a weakened portion disposed between the upper and lower circumferential sleeves.

19. The apparatus of claim 16, wherein the guide members are spaced from one another within the lower circumferential sleeve.

20. A surgical apparatus for removing tissue from an interior portion of a body during a surgical procedure, comprising:

an elongate tubular member having an open distal end and a bore defined therein;

a pouch assembly movable between a proximal location at least partially within the tubular member and a distal location at least partially exterior to the tubular member, the pouch assembly including a support and a pouch removably attached to the support;

the pouch having a first end movable between an open configuration and a closed configuration, and a closed second end;

the pouch including a circumferential sleeve having a plurality of guide members, each guide member of the plurality of guide members having a passage;

a drive member disposed in the bore of the tubular member and attached to the support for moving the pouch assembly from an undeployed position to a deployed position; and a drawstring disposed through each of the passages of the guide members in the circumferential sleeve and forming a loop, the guide members configured to reduce frictional force between the drawstring and circumferential sleeve.

* * * * *